United States Patent
Daly et al.

(10) Patent No.: US 10,786,354 B2
(45) Date of Patent: Sep. 29, 2020

(54) TRANSCATHETER VALVE IMPLANTATION ACCESS SHEATHS

(71) Applicant: St. Jude Medical, Cardiology Division, Inc., St. Paul, MN (US)

(72) Inventors: Jacob John Daly, Blaine, MN (US); Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 342 days.

(21) Appl. No.: 15/704,297

(22) Filed: Sep. 14, 2017

(65) Prior Publication Data

US 2018/0000583 A1    Jan. 4, 2018

Related U.S. Application Data

(62) Division of application No. 14/496,041, filed on Sep. 25, 2014, now Pat. No. 9,788,944.

(60) Provisional application No. 61/893,473, filed on Oct. 21, 2013.

(51) Int. Cl.
*A61F 2/24* (2006.01)

(52) U.S. Cl.
CPC .................. *A61F 2/2436* (2013.01)

(58) Field of Classification Search
CPC ............. A61F 2/2436; A61B 17/3439; A61B 2017/3443; A61M 2025/0024; A61M 2025/0681
See application file for complete search history.

(56) References Cited

U.S. PATENT DOCUMENTS

| | | | | |
|---|---|---|---|---|
| 5,201,756 A | * | 4/1993 | Horzewski | A61M 25/0023 604/104 |
| 5,549,551 A | * | 8/1996 | Peacock, III | A61F 2/958 604/103.05 |
| 5,728,068 A | * | 3/1998 | Leone | A61F 2/958 604/101.01 |
| 6,027,520 A | * | 2/2000 | Tsugita | A61F 2/01 606/200 |
| 6,156,005 A | * | 12/2000 | Theron | A61M 25/104 604/101.05 |

(Continued)

OTHER PUBLICATIONS

Extended European Search Report for Application No. EP14189214.1 dated Mar. 12, 2015.

*Primary Examiner* — Julie A Szpira
(74) *Attorney, Agent, or Firm* — Lerner, David, Littenberg, Krumholz & Mentlik, LLP

(57) ABSTRACT

An introducer provides access to a surgical site in a patient. The introducer includes a proximal housing configured to be positioned outside the patient and a sheath extending from the proximal housing to a distal end of the introducer. One or more handles may be housed at least partially within the proximal housing and configured to translate axially in proximal and distal directions with respect to the proximal housing. A securing element may be slideably coupled to the sheath and may have a flange extending radially outwardly from the sheath. A radially expanding portion of the sheath may have a first edge, a second edge, and a middle section extending from the first edge to the second edge. The sheath portion may have a rolled configuration in which the middle section at least partially overlies the first edge, and the second edge at least partially overlies the middle section.

17 Claims, 9 Drawing Sheets

(56) References Cited

U.S. PATENT DOCUMENTS

| | | | |
|---|---|---|---|
| 6,168,579 B1* | 1/2001 | Tsugita | A61B 17/12109 604/104 |
| 6,443,971 B1* | 9/2002 | Boylan | A61F 2/013 606/200 |
| 6,494,875 B1* | 12/2002 | Mauch | A61F 2/954 604/284 |
| 6,582,448 B1* | 6/2003 | Boyle | A61B 17/12109 606/200 |
| 6,620,148 B1* | 9/2003 | Tsugita | A61B 17/12109 604/509 |
| 6,896,691 B2* | 5/2005 | Boylan | A61F 2/013 606/200 |
| 6,911,039 B2* | 6/2005 | Shiu | A61F 2/95 623/1.12 |
| 7,048,758 B2* | 5/2006 | Boyle | A61B 17/12109 606/200 |
| 7,419,501 B2* | 9/2008 | Chiu | A61F 2/95 623/1.12 |
| 7,780,694 B2* | 8/2010 | Palmer | A61B 17/221 606/200 |
| 2002/0032432 A1* | 3/2002 | Nash | A61M 25/00 604/533 |
| 2002/0165598 A1* | 11/2002 | Wahr | A61B 17/12045 623/1.11 |
| 2002/0183826 A1* | 12/2002 | Dorn | A61F 2/958 623/1.11 |
| 2003/0153943 A1* | 8/2003 | Michael | A61F 2/013 606/200 |
| 2003/0163189 A1* | 8/2003 | Thompson | A61F 2/958 623/1.11 |
| 2004/0199121 A1* | 10/2004 | Wenchell | A61B 17/3421 604/167.06 |
| 2005/0085746 A1 | 4/2005 | Adams et al. | |
| 2006/0015136 A1* | 1/2006 | Besselink | A61F 2/013 606/200 |
| 2006/0030872 A1* | 2/2006 | Culbert | A61B 17/02 606/191 |
| 2006/0041270 A1* | 2/2006 | Lenker | A61B 17/3439 606/198 |
| 2006/0100694 A1* | 5/2006 | Globerman | A61F 2/856 623/1.35 |
| 2006/0135981 A1 | 6/2006 | Lenker et al. | |
| 2007/0255305 A1* | 11/2007 | McMichael | A61B 17/3421 606/191 |
| 2010/0174352 A1* | 7/2010 | Van Der Leest | A61B 17/12136 623/1.11 |
| 2010/0268241 A1* | 10/2010 | Flom | A61B 17/3421 606/104 |
| 2012/0109281 A1* | 5/2012 | Papp | A61F 2/958 623/1.15 |
| 2013/0053792 A1* | 2/2013 | Fischell | A61M 25/0084 604/275 |
| 2013/0297011 A1 | 11/2013 | Morris et al. | |
| 2014/0135909 A1* | 5/2014 | Carr | A61F 2/2436 623/2.11 |

* cited by examiner

TRANSCATHETER VALVE IMPLANTATION ACCESS SHEATHS

CROSS-REFERENCE TO RELATED APPLICATIONS

The present application is a divisional of U.S. patent application Ser. No. 14/496,041, filed Sep. 25, 2014, which claims the benefit of the filing date of U.S. Provisional Patent Application No. 61/893,473 filed Oct. 21, 2013, the disclosures of which are both hereby incorporated herein by reference.

BACKGROUND

The present disclosure relates to prosthetic heart valve replacement and, in particular, delivery systems and introducers for use with prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

Generally, when implanting a prosthetic heart valve into a patient, an introducer sheath is first introduced into the desired blood vessel or other anatomy. This may occur after a guidewire and one or more dilators are introduced into the patient. The introducer sheath is advanced to the site of valve implantation, for example through the apex of the left ventricle to the desired heart valve annulus (transapical) or through the femoral artery to the desired heart valve annulus (transfemoral). As described in greater detail below, other delivery routes for heart valve replacement are possible. Once the introducer sheath is in place, it is used as a conduit to pass other devices, as necessary, from outside the patient to the site of implantation. For example, a delivery device containing the prosthetic heart valve in a collapsed condition may be passed through the introducer sheath so that the prosthetic heart valve may be deployed and implanted at the desired native heart valve annulus.

When the collapsed prosthetic valve has reached the desired implant site in the patient (e.g., at or near the annulus of the heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Generally, introducer sheaths have elongated portions with a hollow core to allow passage of devices through the introducer sheath. Often, the hollow core of the introducer sheath has a diameter that is larger than the largest device that would be passed through the introducer sheath. However, it is generally desired to have the smallest possible diameter for an introducer sheath to accommodate the small and often tortuous anatomy of the vasculature or other delivery route through the body. Additionally, despite different possible routes of delivery, introducer sheaths often have little or no route-dependent variation. It would thus further be desirable to have a single introducer sheath design that could better facilitate delivery of a prosthetic heart valve via different delivery routes.

BRIEF SUMMARY

According to one embodiment of the disclosure, an introducer provides access to a surgical site in a patient. The introducer may include a proximal housing configured to be positioned outside the patient. A sheath has a first portion coupled to the proximal housing and a second portion extending distally of the proximal housing. The second portion has a first edge, a second edge, and a middle section extending from the first edge to the second edge. The second portion has a rolled configuration in which the middle section at least partially overlies the first edge, and the second edge at least partially overlies the middle section.

According to another embodiment of the disclosure, an introducer for providing access to a surgical site in a patient and includes a proximal housing configured to be positioned outside the patient. A sheath extends from the proximal housing to a distal end of the introducer. A first handle is housed at least partially within the proximal housing and is configured to translate axially in a proximal direction and a distal direction with respect to the proximal housing.

According to a further embodiment of the disclosure, an introducer provides access to a surgical site in a patient. The introducer includes a proximal housing configured to be positioned outside the patient and a sheath extending from the proximal housing to a distal end of the introducer. A securing element is slideably coupled to the sheath and has a flange extending radially outwardly from the sheath.

DETAILED DESCRIPTION

As used herein, the term "proximal," when used in connection with an introducer and/or delivery device, refers to an end of the device closer to the user of the device when the device is being used as intended. On the other hand, the term "distal," when used in connection with an introducer and/or delivery device, refers to an end of the device farther away from the user. In the figures, like numbers refer to like or identical parts. As used herein, the terms "substantially," "generally," "approximately," and "about" are intended to mean that slight deviations from absolute are included within the scope of the term so modified. When ranges of values are described herein, those ranges are intended to include sub-ranges. For example, a recited range of 1 to 10 includes 2, 5, 7, and other single values, as well as all sub ranges within the range, such as 2 to 6, 3 to 9, 4 to 5, and others.

Figure 1:
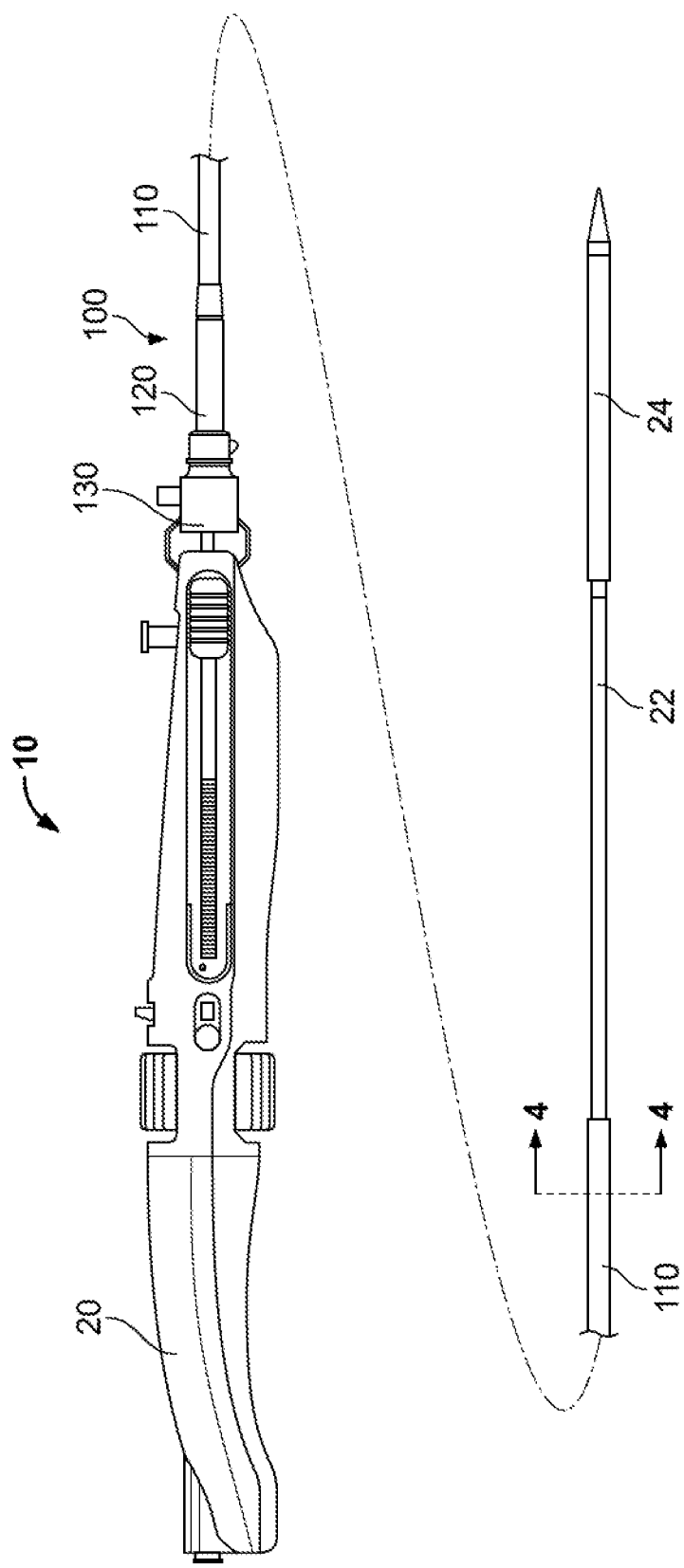
FIG. 1 is a side view of a delivery device for a prosthetic heart valve assembled to an introducer.

FIG. 1 shows a prosthetic heart valve delivery device 10 assembled to an introducer 100. Generally, delivery device 10 includes an operating handle 20 coupled to an outer catheter shaft 22 extending through introducer 100. The delivery device 10 may also include a distal sheath 24 for holding a prosthetic heart valve therein. Introducer 100 may generally include a hollow distal sheath 110 connected to a proximal sheath 120, which in turn is connected to a housing 130.

Figure 2A:
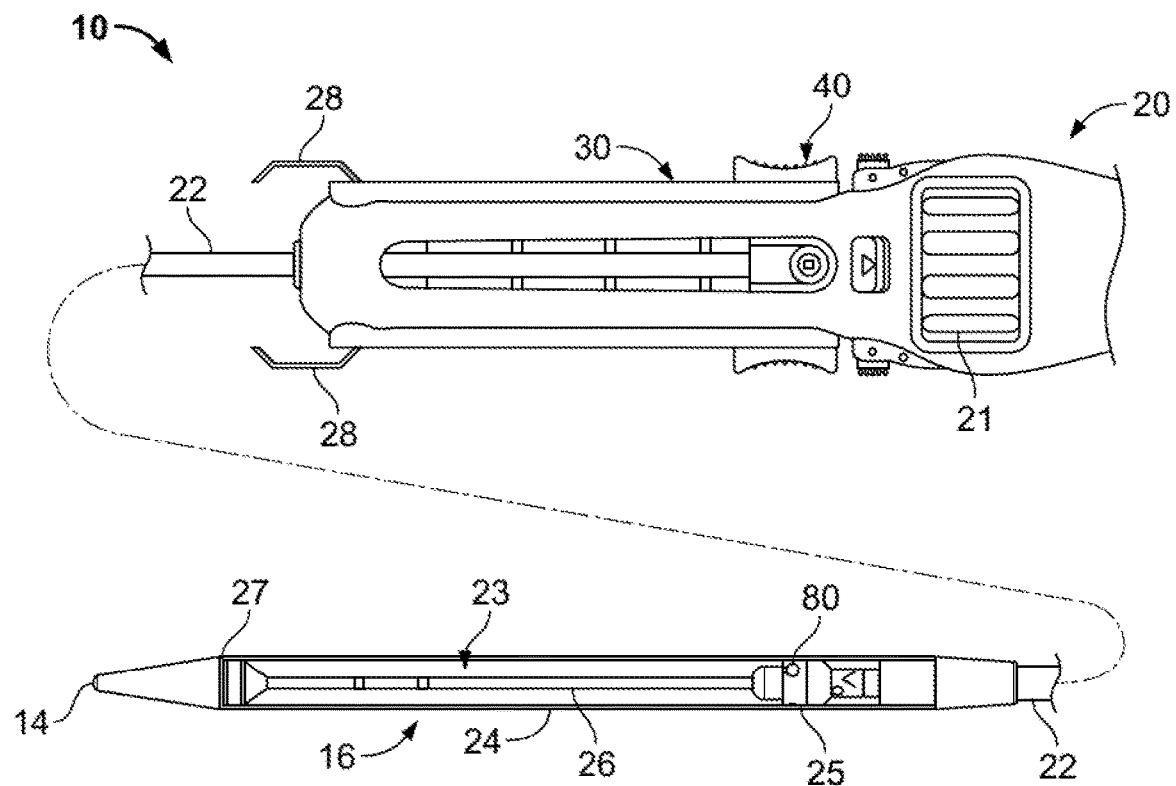
FIG. 2A is a top plan view of a portion of an operating handle for the delivery device of FIG. 1, shown with a partial longitudinal cross-section of the distal portion of a transfemoral catheter assembly.
Figure 2B:
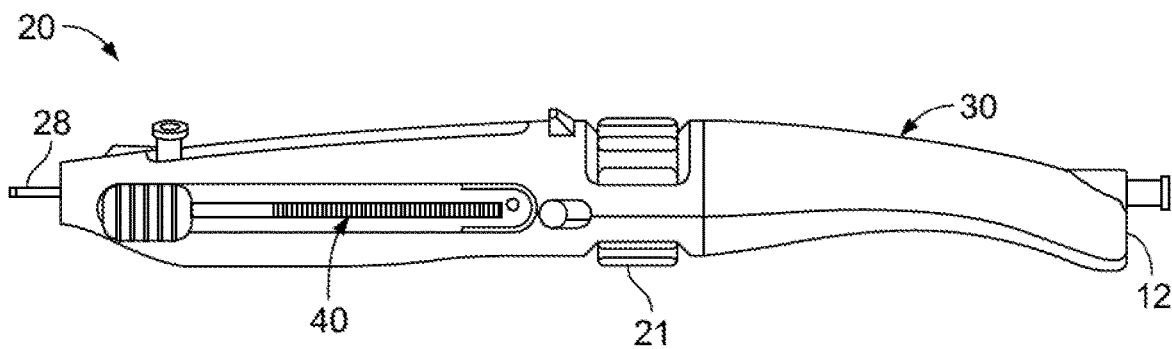
FIG. 2B is a side view of the handle of FIG. 2A.

Referring now to FIGS. 2A-2B, delivery device 10 includes catheter assembly 16 for delivering the heart valve to, and deploying the heart valve at, a target location, and operating handle 20 for controlling deployment of the valve from the catheter assembly. Delivery device 10 extends from proximal end 12 (FIG. 2B) to atraumatic tip 14 at the distal end of catheter assembly 16. Catheter assembly 16 is adapted to receive a collapsible prosthetic heart valve (not shown) in compartment 23 defined around inner shaft 26 and covered by distal sheath 24.

Inner shaft 26 may extend through operating handle 20 to atraumatic tip 14 of delivery device 10, and may include retainer 25 affixed thereto at a spaced distance from tip 14 and adapted to hold a collapsible prosthetic valve in compartment 23. Retainer 25 may have recesses 80 therein that are adapted to hold corresponding retention members of the valve.

Distal sheath 24 surrounds inner shaft 26 and is slidable relative to inner shaft 26 such that it can selectively cover or uncover compartment 23. Distal sheath 24 is affixed at its proximal end to outer shaft 22, the proximal end of which is connected to operating handle 20. The distal end 27 of distal sheath 24 abuts atraumatic tip 14 when the distal sheath is fully covering the compartment 23, and is spaced apart from the atraumatic tip when compartment 23 is at least partially uncovered.

Operating handle 20 is adapted to control deployment of a prosthetic valve located in compartment 23 by permitting a user to selectively slide outer shaft 22 proximally or distally relative to inner shaft 26, thereby respectively uncovering or covering compartment 23 with distal sheath 24. The proximal end of inner shaft 26 may be connected in a substantially fixed relationship to outer housing 30 of operating handle 20, and the proximal end of outer shaft 22 is affixed to carriage assembly 40 that is slidable along a longitudinal axis of the handle housing, such that a user can selectively slide outer shaft 22 relative to inner shaft 26 by sliding carriage assembly 40 relative to the handle housing. For example, a user may rotate deployment actuator 21 to move carriage assembly 40 proximally, thus moving outer shaft 22 and distal sheath 24 proximally to uncover a prosthetic heart valve positioned within compartment 23 in the collapsed condition. As distal sheath 24 begins to clear the prosthetic heart valve, the prosthetic heart valve begins to expand to an expanded condition so that it may be fixed within the native heart valve annulus of interest.

In one embodiment, distal sheath 24 of delivery device 10 may have an outer diameter of between about 18 French and about 19 French. Outer shaft 22 may have an outer diameter of between about 12 French and about 13 French.

The distal end of handle 20 may include a latching element configured to latch or otherwise lock onto a complementary latching element of introducer 100. Although shown in FIGS. 2A-B as a pair of hooks 28, any other suitable latching mechanism, including snaps, knobs, or similar mechanisms may be used, as described in greater detail below. One handle that may be suitable for use is described in greater detail in U.S. Patent Publication No. 2013/0297011, the disclosure of which is hereby incorporated by reference herein.

Figure 3A:
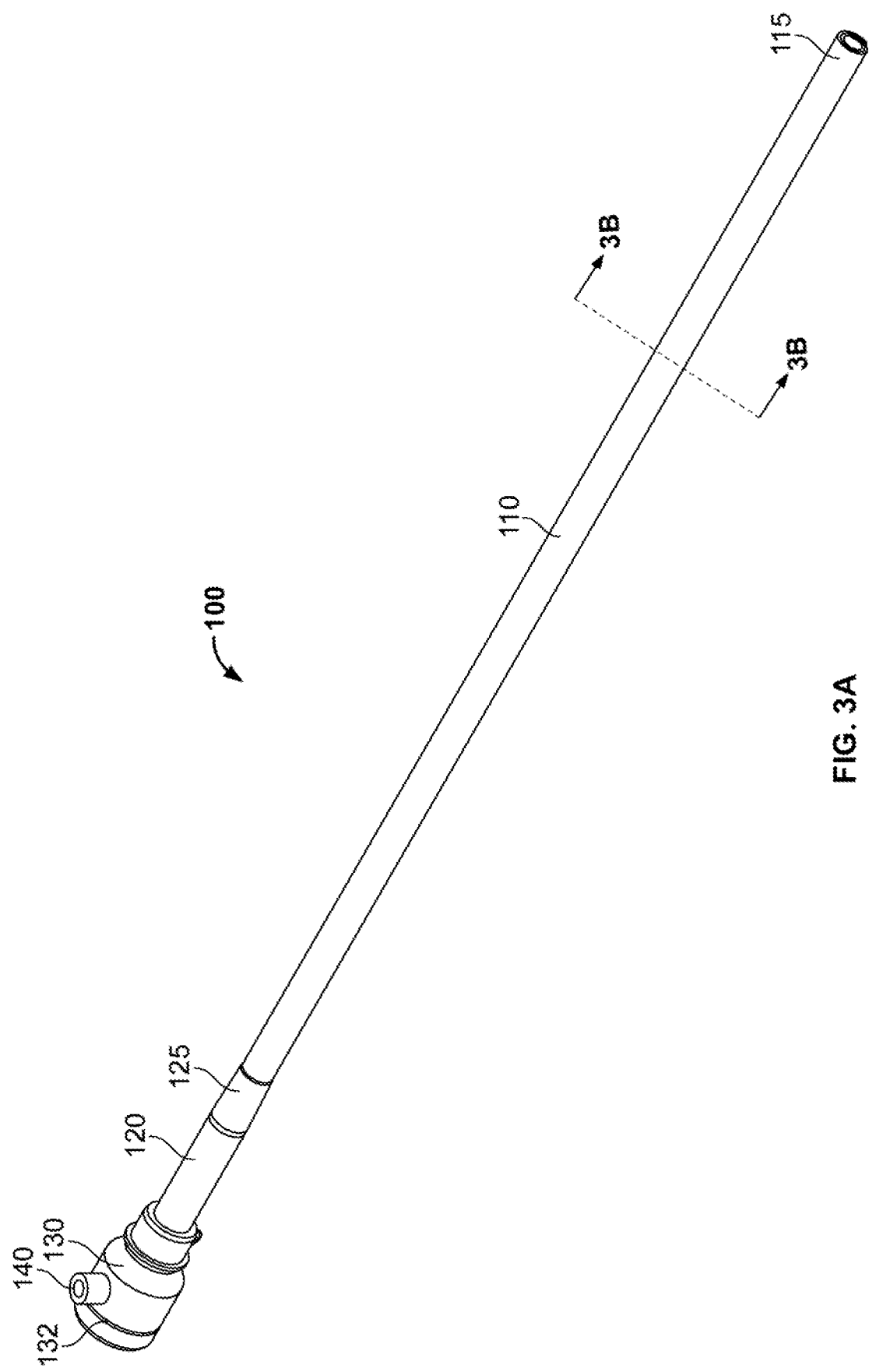
FIG. 3A is a perspective view of the introducer of FIG. 1.

Now referring to FIG. 3A, introducer 100 generally includes a hollow distal sheath 110 connected to a hollow proximal sheath 120. Housing 130 may be connected to proximal sheath 120, and may include additional components including, for example, flush port 140 and one or more seals or hemostasis valves (not illustrated) to prevent blood from flowing proximally out of introducer 100. Housing 130 may also include a latching element 132 complementary to latching element 28 of handle 20. For example, latching element 132 may be a groove, snap, aperture, or other locking mechanism configured to lockingly couple with latching element 28. In one embodiment, proximal sheath 120 may have an outer diameter of approximately 19 French and include a tapered portion at its distal end 125. The distal end 115 of distal sheath 110 may also taper to a reduced diameter.

Figure 3B:
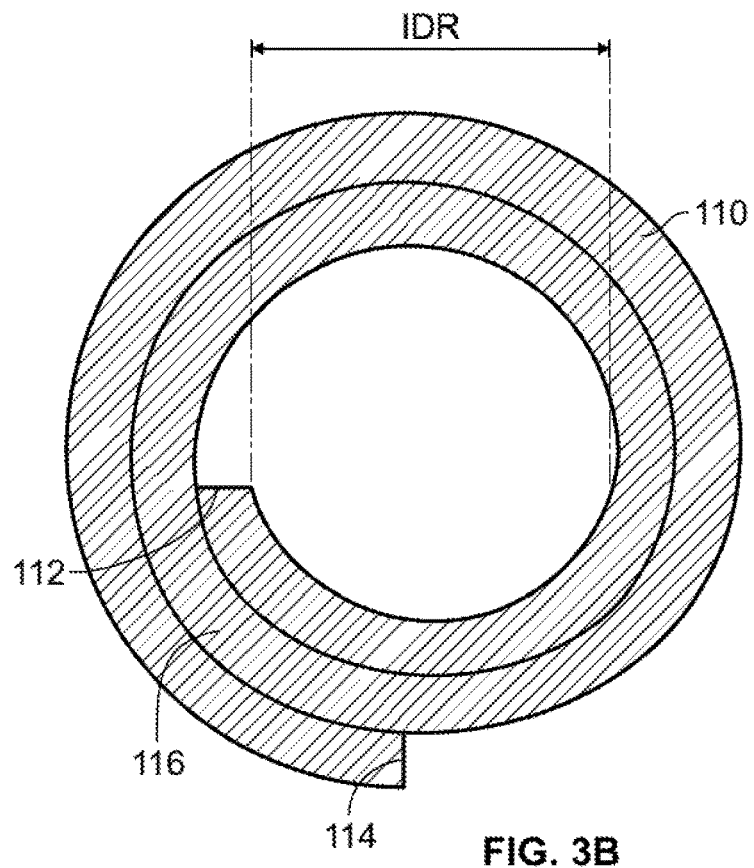
FIG. 3B is a transverse cross-sectional view of the introducer taken along line 3B-3B of FIG. 3A.

FIG. 3B illustrates a transverse cross-section of distal sheath 110 of introducer 100 taken along line 3B-3B in FIG. 3A. Distal sheath 110 may be in a rolled configuration. In other words, distal sheath 110 may include a first edge 112 that is not connected to second edge 114, and a middle section 116 connecting the first edge 112 to the second edge 114. Distal sheath 110 may be rolled so that at least a portion of middle section 116 overlies first edge 112, and second edge 114 overlies at least a portion of middle section 116. Distal sheath 110 may be formed from materials including, but not limited to, polymers, braided materials, coiled materials, Nitinol, silicone, or combinations thereof. Preferably, distal sheath 110 should be formed of a material so that, in the absence of applied force, distal sheath 110 tends to take a configuration similar to the rolled configuration illustrated in FIG. 3B. This may be achieved, for example, by forming distal sheath 110 from Nitinol and heat-setting distal sheath 110 to the rolled configuration. Other materials and processes may also be suitable. For example, extruded polyethylene tubing may be heat-set on a mandrel in the rolled configuration. In one embodiment, in the absence of applied force, distal sheath 110 may have a relaxed inner diameter IDR of less than or equal to about 12 French. With the rolled configuration, distal sheath 110 may radially expand so that the inner diameter of distal sheath 110 increases from the relaxed inner diameter IDR to an expanded inner diameter IDE when an object having a diameter greater than the relaxed inner diameter IDR passes through distal sheath 110.

Figure 4:
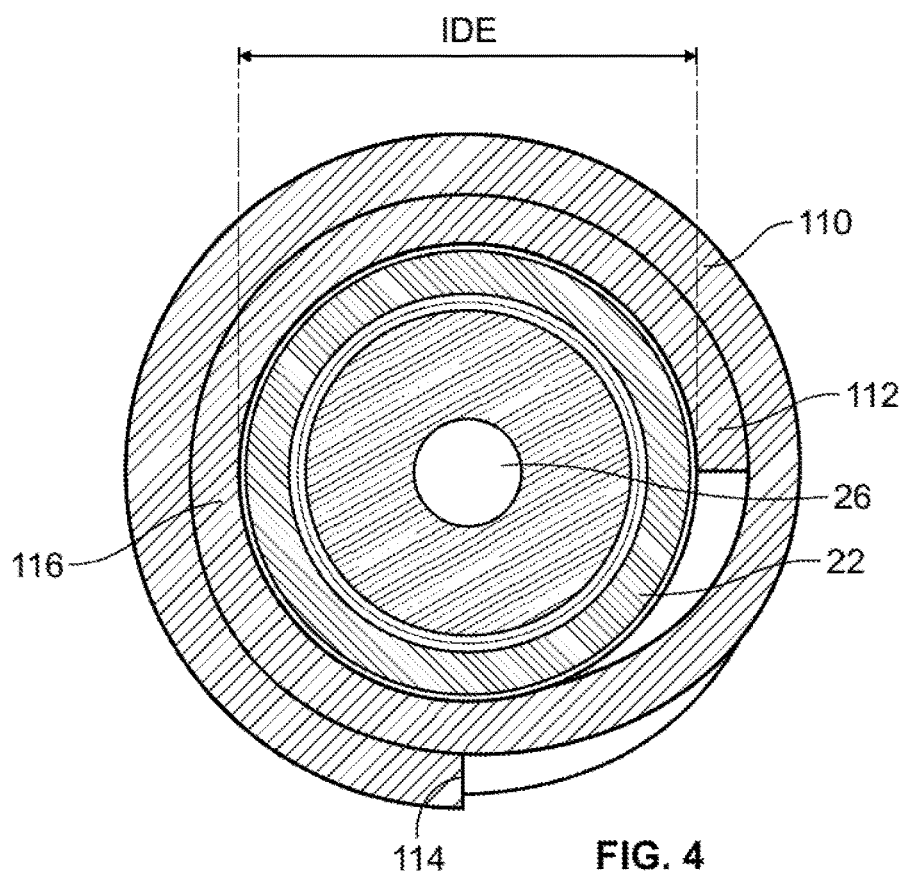
FIG. 4 is a transverse cross-sectional view of the delivery device and introducer assembly taken along line 4-4 of FIG. 1.

For example, FIG. 4 is a transverse cross-section taken along line 4-4 of FIG. 1, and showing a portion of delivery device 10 inserted in introducer 100. When delivery device 10 is inserted into introducer 100, distal sheath 110 of introducer 100 may cover a portion of outer shaft 22 (as well as inner shaft 26) of delivery device 10. If the outer diameter of outer shaft 22 is greater than the relaxed inner diameter IDR of distal sheath 110, distal sheath 110 radially expands by unrolling or unraveling to the expanded inner diameter IDE, which would be substantially equal to the outer diameter of outer shaft 22. In some embodiments, the distal sheath 24 of delivery device 10 has the largest outer diameter of all the portions of catheter assembly 16 intended for insertion into a patient. For example, in the embodiment in which outer shaft 22 has an outer diameter of between about 12 French and about 13 French, the outer diameter of distal sheath 24 may be between about 18 French and about 19 French. In this case, it is preferable that the distal sheath 110 of introducer 100 be capable of expanding from a relaxed inner diameter IDR of about 12 French to an expanded inner diameter IDE of between about 18 French and about 19 French, as is described in greater detail below. However, it should be understood that these are just illustrative values. For example, the distal sheath 110 of introducer 100 may be capable of radially expanding to an expanded inner diameter IDE of up to about 21 French or more.

According to an aspect of the disclosure, introducer 100 may be assembled to delivery device 10 prior to insertion of the assembly into a patient. For example, the tip 14 of delivery device 10 may be inserted through housing 130, proximal sheath 120, and distal sheath 110 of introducer 100, until housing 130 is adjacent a distal end of operating handle 20. As delivery device 10 passes through introducer 100, distal sheath 110 radially expands from its relaxed inner diameter IDR to a first expanded inner diameter IDE substantially equal to the outer diameter of the distal sheath 24 of delivery device 10. After the distal sheath 24 of the delivery device 10 clears introducer 100, the distal sheath 110 of introducer 100 radially contracts or relaxes to a second expanded inner diameter IDE substantially equal to the outer diameter of the outer shaft 22 of delivery device 10. This expansion and contraction is possible at least in part due to the rolled configuration and material properties of distal sheath 110, as described above. In the assembled configuration, the tapered portion at the distal end 115 of distal sheath 110 may help provide a fluid-tight seal between introducer 100 and the outer shaft 22 of delivery device 10. Similarly, the tapered portion at distal end 125 of proximal sheath 120 may help provide a fluid-tight seal between proximal sheath 120 and distal sheath 110. Proximal sheath 120 may be coupled to distal sheath 110 in any suitable manner. For example, proximal sheath 120 and distal sheath 110 may be created from a single tube of material, with a slit made along the longitudinal length of the distal sheath 110. Distal sheath 110 may be placed around a mandrel or similar device and heat set such that, in the absence of applied forces, it is in a rolled configuration. In this case, proximal sheath 120 may be coupled to housing 130 and biocompatible elastomer or other suitable covering may be fit over at least the transition from the cylindrical proximal sheath 120 to the rolled distal sheath 110. Alternatively, a sheath may be formed as described immediately above, with a separate proximal sheath 120 placed over the transition from a straight distal tube portion to rolled distal sheath 110. In this case, some portion of rolled distal sheath 110 may reside inside proximal sheath 120. Taper 125 may be covered with a biocompatible elastomer or other suitable material to provide a smooth transition and to help keep the transition fluid tight. In addition, an expandable outer layer of material may surround part or all of distal sheath 110, for example to help provide a fluid seal around distal sheath 110 and prevent fluid leakage between the layers of the sheath. The expandable outer layer may provide a smooth outer surface, and may also help prevent devices from protruding through distal sheath 110 between first and second edges 112 and 114 as distal sheath 110 expands. The expandable outer layer may be formed from a biocompatible elastomer such as Chronarene provided by AdvanSource Biomaterials, although other expandable materials may be suitable.

Once the housing 130 of introducer 100 is substantially adjacent to the distal end of operating handle 20, introducer 100 and delivery device 10 are in a fully assembled condition, as shown in FIG. 1. If desired, the latching mechanism 28 of operating handle 20 may be connected to the complementary latching mechanism 132 of introducer 100 so that delivery device 10 and introducer 100 are in locked configuration with respect to one another. If the surgeon desires introducer 100 to be freely moveable with respect to delivery device 10, he may leave the complementary latching mechanisms 28 and 132 unconnected. In the assembled condition, a prosthetic heart valve may be inserted into the compartment 23 of delivery device 10 in a collapsed condition. It should be noted that the prosthetic heart valve may be positioned within compartment 23 prior to inserting delivery device 10 into introducer 100. With delivery device 10 assembled to introducer 100, and with the prosthetic heart valve loaded in compartment 23 in the collapsed condition and covered by distal sheath 24, a surgeon may introduce delivery device 10 into the patient, for example via the femoral artery. Once the prosthetic heart valve is positioned at the site of implantation, it may be released from delivery device 10 as described above. Delivery device 10 and introducer 100 may then be removed from the patient while still in the assembled condition.

The use of introducer 100 with the procedure described above may have a number of benefits. For example, if the surgeon wants or needs to insert another device to the site of implantation, such as another delivery device or an interventional device such as an expandable balloon, he can remove delivery device 10 while leaving introducer 100 in place. As delivery device 10 is removed from the body, the distal sheath 110 of introducer 100 radially expands as necessary to permit the withdrawal of delivery device 10. Once delivery device 10 has been removed, the surgeon may introduce another device to the site of implantation by advancing that device through introducer 100, which provides a path to the site of implantation. Further, use of an expandable distal sheath 110 allows introducer 100 to have a relatively small outer diameter, which may reduce vascular complications. Generally, smaller diameters are more preferred for devices being passed through the vasculature. If it became necessary to withdraw delivery device 10 from the patient so that another device could be inserted through the non-expandable introducer, the introducer would only permit such withdrawal if the inner diameter of the introducer was greater than the largest diameter of the catheter assembly 16 of delivery device 10. If a non-expandable introducer were used with delivery device 10, it would need to have an inner diameter greater than the outer diameter of distal sheath 24. Even further, assembling introducer 100 to delivery device 10 prior to inserting the assembly into the patient may allow for a reduced diameter of the assembly as the assembly is advanced to the site of implantation. For example, if the procedure is completed without removing the delivery device 10 from the introducer 100, the greatest outer diameter experienced by the assembled device is the outer diameter of distal sheath 24 (assuming the largest outer diameter of introducer 100 is less than the outer diameter of distal sheath 24). On the other hand, if introducer 100 were first advanced to the site of implantation with delivery device 10 later advanced through introducer 100, the greatest outer diameter experienced within the vasculature would be the outer diameter of distal sheath 24 plus the thickness of additional material of distal sheath 110 surrounding distal sheath 24 as delivery device 10 passes through the introducer 100. The provision of the complementary locking mechanisms 28 and 132 may also simplify advancement of the delivery device 10 and deployment of the prosthetic heart valve, as the surgeon may not need to manage each device separately once they are locked together.

Although a heart valve replacement procedure is described above with reference to advancement of delivery device 10 and introducer 100 through the femoral artery to the site of implantation, other deliver routes may be desirable. For example, a collapsible prosthetic heart valve may be delivered with a similar or identical delivery device as described above with delivery directly through the apex of the left ventricle (transapical), directly through the aortic artery (transaortic), through the subclavian artery, or through the axillary artery. Previously, whether delivering a collapsible prosthetic heart valve via the transfemoral approach or an alternative approach (including transapical, transaortic, subclavian, and axillary), an introducer sheath designed for the transfemoral approach, with possible minor variations, was used. While this strategy reduced complexity, the use of an introducer sheath created for transfemoral delivery may not be optimal for alternative delivery routes. For example, the tortuosity of the subclavian and axillary arteries may make introducer sheaths more prone to kinking compared to transfemoral delivery. Similarly, an introducer with a completely straight distal sheath may not be ideal for all delivery routes. For example, while transaortic delivery may occur along a relatively straight path through the body to the site of implantation, an introducer with an angle may be preferable for other routes to center the delivery device within the native heart valve. This might be the case for transfemoral delivery, which generally requires the introducer to bend around the aortic arch, or transapical delivery, in which the center of the native valve annulus does not align with the apex of the heart.

Figure 5A:
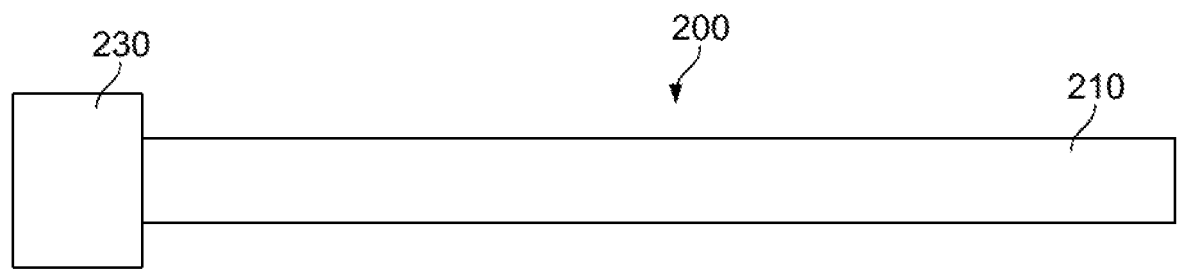
FIG. 5A is a schematic side view of an introducer according to an embodiment of the disclosure.
Figure 5B:
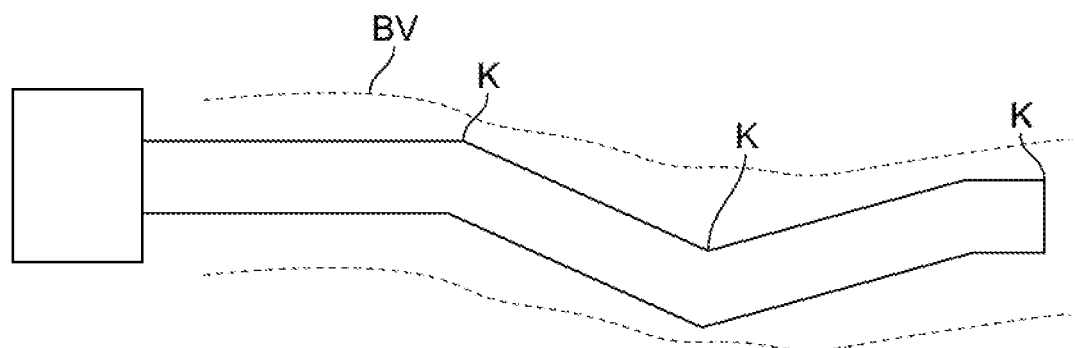
FIG. 5B is a schematic side view of a prior art introducer during use within the vasculature.
Figure 5C:
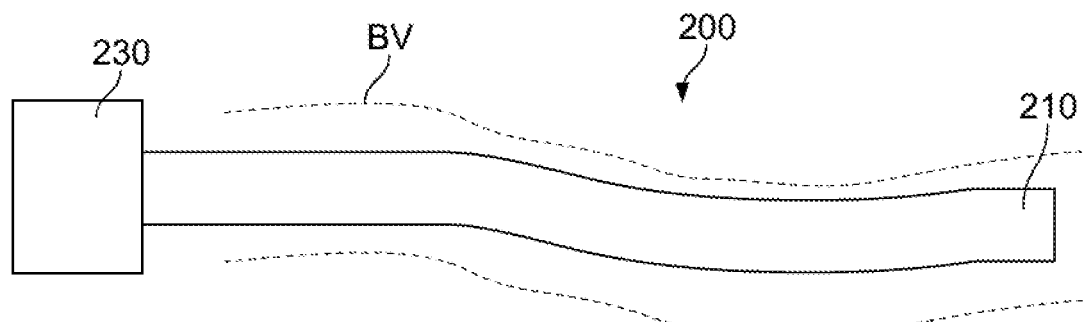
FIG. 5C is a schematic side view of the introducer of FIG. 5A during use within the vasculature.

Referring to FIG. 5A, an introducer 200 includes a housing 230 and a distal sheath 210. Introducer 200 may be the same as introducer 100 described in connection with FIGS. 3A-B. Alternately, introducer 200 may include a generally tubular non-expandable distal sheath 210. Although not illustrated in FIG. 5A, introducer 200 may also include a separate proximal sheath, flush ports, hemostatic valves and/or seals, and the like. As noted above, distal sheath 210 may be prone to kinking as it advances through the vasculature, particularly vasculature with relatively high tortuosity. Kinks may become a larger problem as introducer sheaths become thinner Thinner introducer sheaths may be preferable to maximize the inner diameter of the introducer while minimizing the outer diameter of the introducer. As shown in FIG. 5B, as an introducer passes through a blood vessel BV, it may develop one or more kinks K along the sheath. Kinks K may make it difficult for a delivery device to pass through the introducer sheath to the site of implantation. Although an introducer prone to kinking may not be problematic for the relatively straight path of a transaortic delivery route, for example, it may not be suitable for the more tortuous subclavian or axillary delivery routes. To increase kink resistance, distal sheath 210 may be formed from a polymer such as Pebax co-extruded or braided with stainless steel wire or coil. Similarly, a metal tube, such as a Nitinol tube, may be cut longitudinally along the length thereof and provided with a number of slots or cut-outs to provide flexibility. The metal tube may be impregnated with a polymer such as Pebax to form distal sheath 210. In this case, a liner or other material may be provided on an inner and/or outer surface of the polymer and tube to provide a smooth surface. Further, the material forming distal sheath 210, whether a polymer or other material, may be braided or coiled to increase kink resistance. In addition, with a braided and/or coiled distal sheath 210, kink resistance increases as distal sheath 210 is more likely to conform to the turns and bends in the blood vessel BV, as shown in FIG. 5C.

Figure 5D:
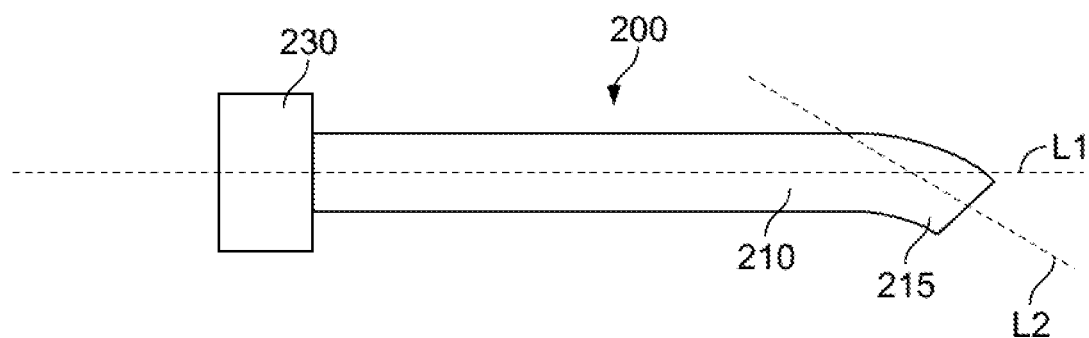
FIG. 5D is a schematic side view of the introducer of FIG. 5A with a deflected tip.

Introducer 200 may additionally or alternatively include pull wires (not shown) extending from a distal end 215 of distal sheath 210 to a proximal end of introducer 200 that can be manipulated from outside the patient. For example, pull wires may pass through one or more channels formed longitudinally in the walls of distal sheath 210. As shown in FIG. 5D, the pull wires may be manipulated by the surgeon to deflect the distal end 215 of distal sheath 210 so that a longitudinal axis L1 of a proximal portion of distal sheath 210 and a longitudinal axis L2 of the distal end 215 of distal sheath 210 form an oblique angle with respect to one another. By using such pull wires to deflect the distal end 215 of distal sheath 210, it may be easier to align the distal end 215 of distal sheath 210 with the center of the native valve annulus of the heart valve being replaced.

In addition or as an alternate to using a deflectable introducer 200, it may be beneficial to use a deflectable dilator. When introducing devices to the site of implantation, a thin guidewire may be the first device advanced through the vasculature to the site of implantation. A dilator may then be assembled over the guidewire and advanced to the site of implantation. If desired, additional dilators of increasing size may be passed over dilators of smaller sizes or may be inserted over the guidewire following removal of the previously inserted dilator. Once a large enough dilator is in place, introducer 200 may be advanced over the dilator to the site of implantation. The dilator(s) may include pull wires to provide for deflection similar to the introducer 200 of FIG. 5D. By deflecting the dilator, it may be easier for the introducer 200 to be initially placed at the site of implantation in alignment with the center of the native valve annulus of the heart valve being replaced. It should be clear that a non-deflectable introducer may be placed over a deflectable dilator, with deflection of the dilator being translated to the introducer overlying the dilator.

Figure 5E:
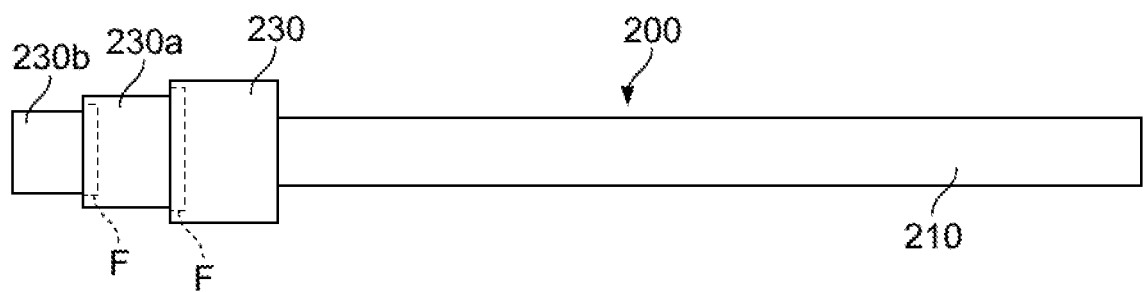
FIG. 5E is a schematic side view of the introducer of FIG. 5A with handle portions in an extended configuration.

Referring now to FIG. 5E, introducer 200 may alternately or additionally include an adjustable length handle. Housing 230, in addition to including hemostatic valves, seals, and/or other similar components, may house one or more extendable handle portions at least partially therein, such as handle portions 230*a* and 230*b*. The handle portions 230*a* and 230*b* may slide proximally out of housing 230 in a telescoping fashion, for example by manually pulling the handle portions 230*a* and 230*b* proximally. Each handle portion 230*a* and 230*b* may include a flange F at a distal end to act as a stop to limit the distance the handle portion may be pulled proximally with respect to other handle portions. However, other stop mechanisms may be suitable. In addition, each handle portion 230a and 230b may include a locking element. For example, flange F of handle portion 230b may include threads configured to mate with corresponding threads on the internal surface at the proximal end of handle portion 230a. Once in the extended condition, shown in FIG. 5E, a user may rotate handle portion 230b to lock handle portion 230b from sliding axially with respect to handle portion 230a. Handle portion 230a may include a similar locking element configured to mate with a complementary locking element in housing 230. If more than two extendable handle portions 230a and 230b are desired, those additional portions may also include locking elements.

Figure 5F:
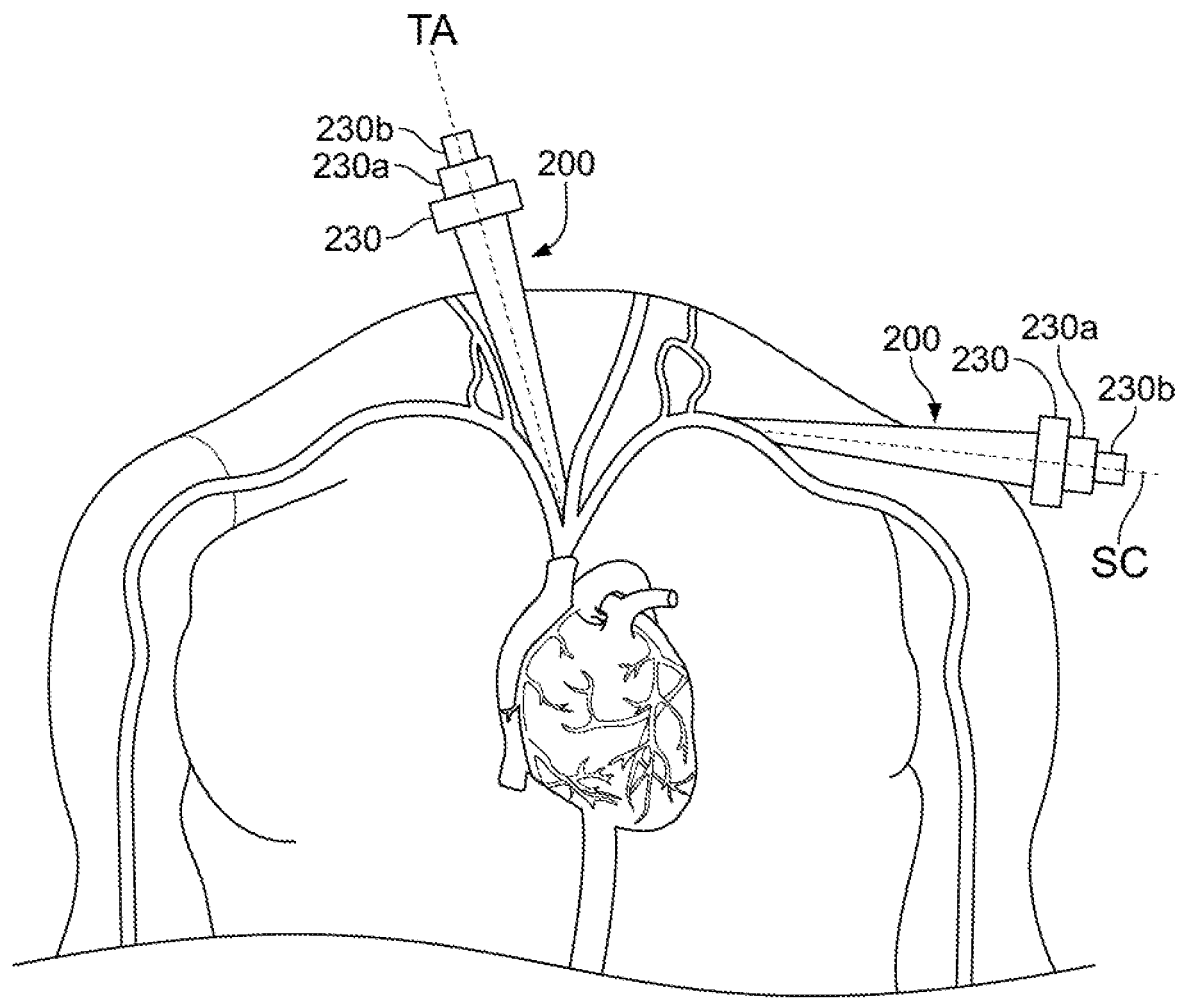
FIG. 5F is a diagram of the introducer of FIG. 5A delivered through the aortic artery and the subclavian artery with handle portions in the extended configuration.

The inclusion of extendable handle portions 230a and 230b in introducer 200 may provide the ability for a surgeon to avoid placing his hand in a radiation field during a heart valve replacement procedure. For example, during heart valve replacement, an x-ray field may be applied around the site of implantation to allow the surgeon to visualize the heart as well as surgical components in real time. With some delivery routes, such as a transfemoral delivery, the surgeon is relatively far away from the heart and thus from the radiation field. However, as shown in FIG. 5F, if introducer 200 is inserted via a transaortic delivery route TA or via a subclavian delivery route SC, housing 230 may be in close proximity to the surgical site, and thus close to or within the radiation field. This may be problematic because during manipulation of introducer 200, housing 230 is generally gripped or held by the user, for example when inserting another device through introducer 200. If the particular delivery route used results in housing 230 being in or close to the radiation field, the surgeon may extend the housing 230 proximally by pulling handle portions 230b and 230a proximally in a telescoping fashion. Once the handle portions are extended, the surgeon may twist or rotate the handle portions 230a and/or 230b to lock them in place. In the locked condition, the surgeon can handle introducer 200 while, for example, inserting a delivery device through the introducer 200, without the extendable handle portions 230a and 230b moving unintentionally. It should be noted that in FIG. 5F, although introducer 200 is shown delivered through the aortic artery as well as the subclavian artery, generally only a single introducer 200 would be used via a single delivery route in any given heart valve replacement procedure.

Figure 5G:
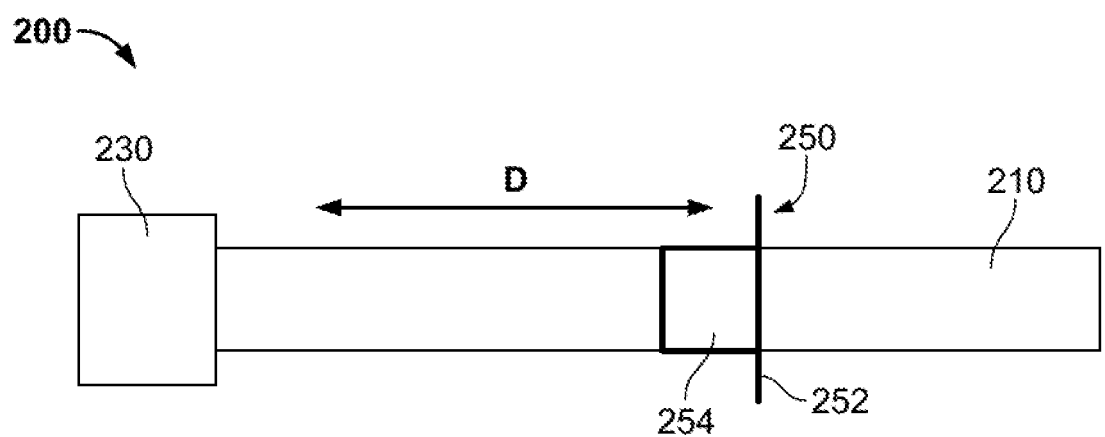
FIGS. 5G and 5H are schematic side and perspective views, respectively, of the introducer of FIG. 5A with a securing element coupled thereto.
Figure 5H:
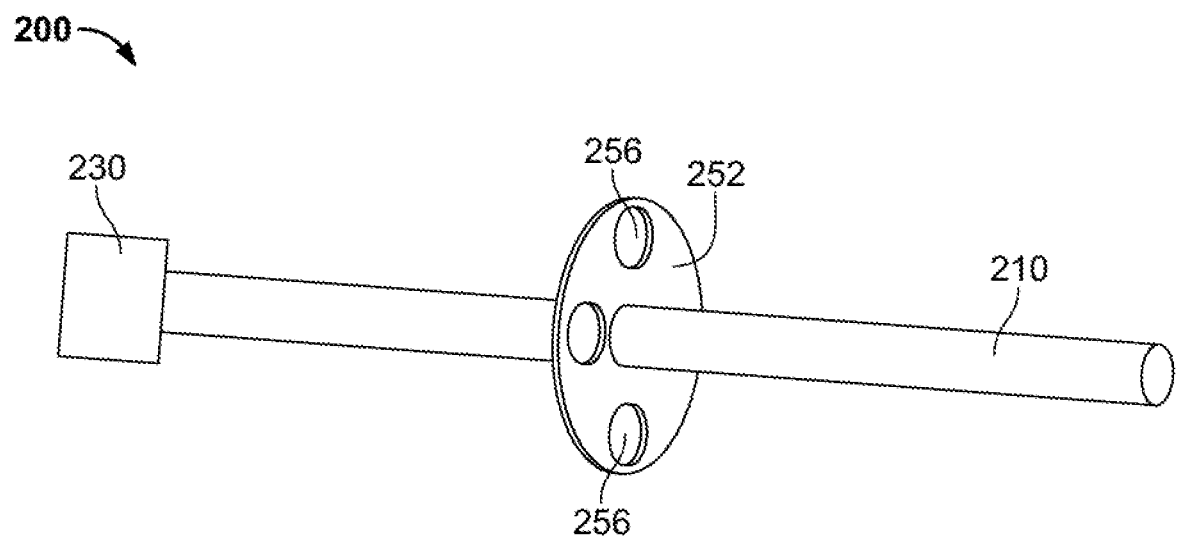

Introducer 200 may also include a securing element 250. As shown in FIGS. 5G-H, securing element 250 may include a cylindrical handle 254 assembled over distal sheath 210 and a flange 252 extending radially outwardly from handle 254 and from distal sheath 210. The fit between handle 254 and distal sheath 210 may be loose enough so that application of force slides securing element 250 axially along distal sheath 210 in the proximal or distal directions indicated by the arrows D, while being tight enough that securing element 250 is unlikely to slide unintentionally. Alternately or in addition, handle 254 may include a locking mechanism to lock securing member 250 from axial movement with respect to distal sheath 210. For example, handle 254 may include a simple set screw arrangement or an internal split nut structure that may lockingly clamp over distal sheath 210 upon rotation of handle 254. Other locking mechanisms may also be suitable. For example, a rotating collar that tightens down on handle 254 when rotated, for example via a threaded connection, may also be suitable for the locking mechanism. Flange 252 may include a plurality of apertures 256 therethrough to allow for securing flange 252 to native anatomy, for example by suturing flange 252 to the vasculature. Flange 252 may be formed of a flexible material so that it better conforms to the surface of the anatomy to which it is being secured.

Figure 5I:
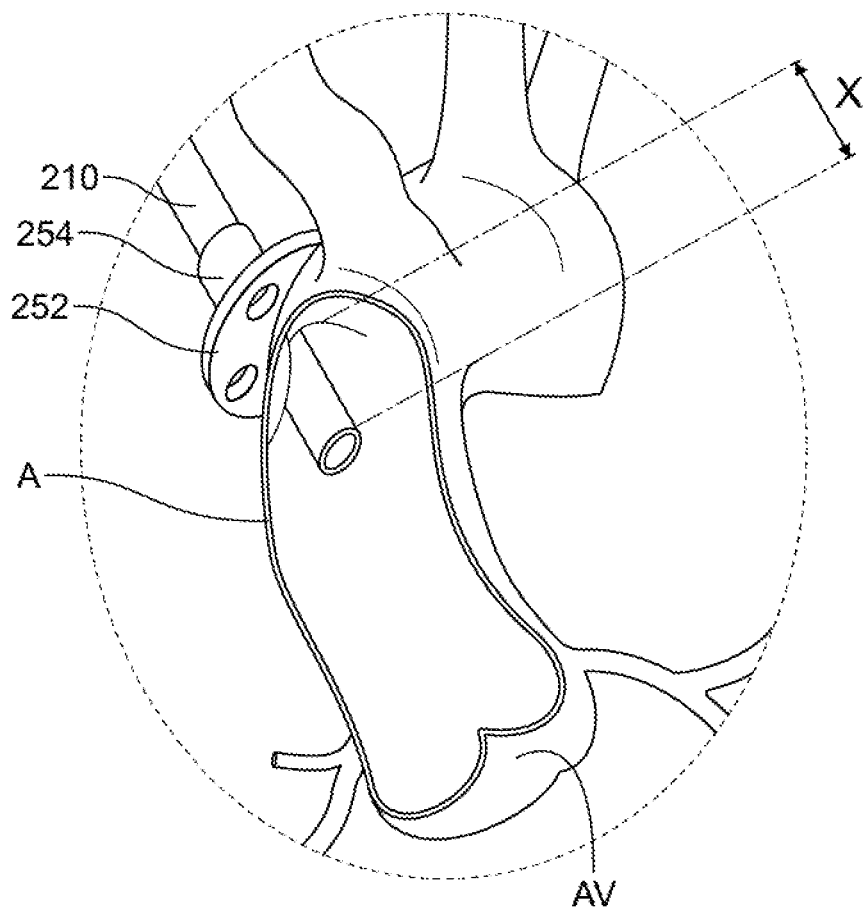
FIG. 5I is a cutaway view of the introducer of FIG. 5A inserted into the aorta with the securing element coupled to the aorta.

Securing member 250 may be particularly useful when implanting a prosthetic heart valve via the transaortic delivery route. As shown in FIG. 5I, during a transaortic prosthetic heart valve replacement procedure, introducer 200, and specifically distal sheath 210, may be passed a relatively short distance X into aorta A. During an aortic valve replacement procedure, there may be relatively little working space between the point of entry of distal sheath 210 in aorta A and the aortic valve AV. Thus, slight movement of introducer 200 proximally may result in introducer 200 exiting the aorta A, while slight movement of introducer 200 distally may reduce the amount of working space and cause difficulties in completing the procedure. Once introducer 200 is advanced the desired distance X into aorta A, the surgeon may slide securing member 250 distally until flange 252 abuts the external surface of aorta A. When in this position, the surgeon may lock securing member 250 from additional sliding motion relative to distal sheath 210, for example by rotating handle 254, and then pass sutures through apertures 256 and aorta A to secure flange 252 to aorta A. Once suturing is complete, distal sheath 210 is positioned the desired distance X into aorta A and cannot readily move proximally or distally with respect to aorta A until the sutures are removed and/or securing member 250 is unlocked with respect to distal sheath 210. This may reduce the complexity of the surgery by allowing the surgeon to concentrate more fully on the valve implantation without worrying about introducer 200 being moved during the procedure.

It should be noted that delivery devices other than delivery device 10 may be suitable for use with the introducers described above. For example, delivery device 10 may be suitable for a transfemoral aortic valve implantation, but may not be suitable for a transapical aortic valve implantation. A modified version of delivery device 10 for transapical aortic valve implantation may still, however, be used with the introducers described herein. Additionally, any of the components described above with respect to introducers 100 and 200 may include radiopaque markers, such as radiopaque rings, to better visualize the position of the component within the body during any given procedure, for example by using X-ray fluoroscopy. It should further be noted that introducers 100, 200 can be used for other laparoscopic or percutaneous medical procedures including angioplasty, stent implantation, laparoscopic surgery, etc.

According to one embodiment of the disclosure, an introducer for providing access to a surgical site in a patient comprises:
  a proximal housing configured to be positioned outside the patient; and
  a sheath having a first portion coupled to the proximal housing and a second portion extending distally of the proximal housing, the second portion having a first edge, a second edge, and a middle section extending from the first edge to the second edge,
  wherein the second portion has a rolled configuration in which the middle section at least partially overlies the first edge, and the second edge at least partially overlies the middle section; and/or
  the second portion of the sheath is radially expandable from a relaxed inner diameter to an expanded inner diameter greater than the relaxed inner diameter; and/or
  the relaxed diameter is less than or equal to about 12 French; and/or the second portion of the sheath is radially expandable to an inner diameter of between about 18 French and about 19 French; and/or the second portion of the sheath is radially expandable to an inner diameter of about 21 French; and/or the second portion of the sheath is formed of a braided material; and/or a system for delivering a collapsible prosthetic heart valve to the surgical site in the patient further comprises a delivery device assembled to the introducer and having a handle and a catheter assembly extending distally from the handle, wherein the introducer surrounds at least a portion of the catheter assembly; and/or the catheter assembly includes a proximal catheter shaft having a first outer diameter and a distal catheter shaft having a second outer diameter larger than the first outer diameter, the distal catheter shaft being configured to house the collapsible prosthetic heart valve in a collapsed condition; and/or the second portion of the sheath has a relaxed inner diameter that is radially expandable to expanded inner diameter that is greater than the second outer diameter of the distal catheter shaft.

According to another embodiment of the disclosure, an introducer for providing access to a surgical site in a patient comprises:

a proximal housing configured to be positioned outside the patient;

a sheath extending from the proximal housing to a distal end of the introducer; and a first handle housed at least partially within the proximal housing and configured to translate axially in a proximal direction and a distal direction with respect to the proximal housing; and/or a second handle housed at least partially within the proximal housing and at least partially within the first handle, the second handle being configured to translate axially in the proximal direction and the distal direction with respect to the proximal housing and the first handle; and/or a first locking element on the first handle and a second locking element on the proximal housing, the first locking element configured to engage the second locking element to restrict axial translation of the first handle with respect to the proximal housing; and/or the first locking element is a first thread and the second locking element is a second thread configured to mate with the first thread; and/or a flange on a distal end of the first handle and configured to limit axial translation of the first handle in the proximal direction with respect to the proximal housing.

In a further embodiment of the disclosure, an introducer for providing access to a surgical site in a patient comprises:

a proximal housing configured to be positioned outside the patient;

a sheath extending from the proximal housing to a distal end of the introducer; and a securing element slideably coupled to the sheath, the securing element having a flange extending radially outwardly from the sheath; and/or the flange includes a plurality of apertures extending therethrough; and/or the flange is flexible; and/or the securing element has a handle portion coupled to the flange and a locking element configured to restrict sliding motion of the sealing element with respect to the sheath.

Although the invention herein has been described with reference to particular embodiments, it is to be understood that these embodiments are merely illustrative of the principles and applications of the present invention. For example, features described in connection with one embodiment may be combined with features described in connection with another embodiment without varying from the scope of the invention. It is therefore to be understood that numerous modifications may be made to the illustrative embodiments and that other arrangements may be devised without departing from the spirit and scope of the present invention as defined by the appended claims.

The invention claimed is:

1. An introducer for providing access to a surgical site in a patient comprising:
   a proximal housing configured to be positioned outside the patient;
   a sheath extending from the proximal housing to a distal end of the introducer;
   a first handle housed at least partially within the proximal housing and configured to translate axially in a proximal direction and a distal direction with respect to the proximal housing; and
   at least one pull wire extending from a distal end of the sheath to a proximal end of the introducer,
   wherein the proximal housing and first handle together form at least part of an adjustable-length handle,
   wherein the at least one pull wire passes through one or more channels formed longitudinally in a wall of the sheath.

2. The introducer of claim 1, further comprising a flange on a distal end of the first handle and configured to limit axial translation of the first handle in the proximal direction with respect to the proximal housing, wherein when the flange is in an engaged condition in which the first handle is limited from axial translation in the proximal direction with respect to the proximal housing, a distalmost end of the proximal housing is positioned distal to a proximalmost end of the first handle.

3. The introducer of claim 1, further comprising a first locking element on the first handle and a second locking element on the proximal housing, the first locking element configured to engage the second locking element to restrict axial translation of an entirety of the first handle with respect to an entirety of the proximal housing.

4. The introducer of claim 3, wherein the first locking element is a first thread and the second locking element is a second thread configured to mate with the first thread.

5. The introducer of claim 1, further comprising a second handle housed at least partially within the proximal housing and at least partially within the first handle, the second handle being configured to translate axially in the proximal direction and the distal direction with respect to the proximal housing and the first handle such that the proximal housing, the first handle, and the second handle together form the adjustable-length handle.

6. The introducer of claim 5, further comprising a flange on a distal end of the second handle and configured to limit axial translation of the second handle in the proximal direction with respect to the first handle.

7. The introducer of claim 5, further comprising a first locking element on the second handle and a second locking element on the first handle, the first locking element configured to engage the second locking element to restrict axial translation of the second handle with respect to the first handle.

8. The introducer of claim 1, wherein the sheath is formed of a polymer.

9. The introducer of claim 1, wherein the sheath is formed of a metal tube.

10. The introducer of claim 9, wherein the metal tube includes a plurality of longitudinal slots formed therein.

11. The introducer of claim 10, wherein the metal tube is impregnated with a polymer.

12. The introducer of claim 11, further comprising a liner positioned on at least one of an inner surface and an outer surface of the sheath.

13. The introducer of claim 1, wherein the sheath is formed of a braided polymer or a braided metal.

14. An introducer for providing access to a surgical site in a patient comprising:
- a proximal housing configured to be positioned outside the patient;
- a sheath extending from the proximal housing to a distal end of the introducer;
- a first handle housed at least partially within the proximal housing and configured to translate axially in a proximal direction and a distal direction with respect to the proximal housing; and
- at least one pull wire extending from a distal end of the sheath to a proximal end of the introducer,
- wherein the proximal housing and first handle together form at least part of an adjustable-length handle,
- wherein the at least one pull wire has a manipulated condition in which a proximal portion of the sheath extends along a first longitudinal axis and the distal end of the sheath extends along a second longitudinal axis oblique to the first longitudinal axis.

15. An introducer for providing access to a surgical site in a patient comprising:
- a proximal housing configured to be positioned outside the patient;
- a sheath extending from the proximal housing to a distal end of the introducer;
- a first handle housed at least partially within the proximal housing and configured to translate axially in a proximal direction and a distal direction with respect to the proximal housing; and
- a securing element slideably coupled to the sheath, the securing element having a flange extending radially outwardly from the sheath,
- wherein the proximal housing and first handle together form at least part of an adjustable-length handle,
- wherein the flange of the securing element includes a plurality of apertures extending therethrough.

16. The introducer of claim 15, wherein the flange is flexible.

17. The introducer of claim 15, wherein the securing element has a handle element coupled to the flange of the securing element, and a lock configured to restrict sliding motion of the sealing element with respect to the sheath.

* * * * *